United States Patent [19]

Schmid et al.

[11] Patent Number: 4,907,596
[45] Date of Patent: Mar. 13, 1990

[54] BLOOD PRESSURE MEASURING APPLIANCE

[75] Inventors: Walter Schmid, Fuchsweg 9, D-7914 Pfaffenhofen; Bernhard Schwab, Buxheim, both of Fed. Rep. of Germany

[73] Assignee: Walter Schmid, Pfaffenhofen, Fed. Rep. of Germany

[21] Appl. No.: 910,487

[22] Filed: Sep. 23, 1986

[30] Foreign Application Priority Data

Sep. 23, 1985 [DE] Fed. Rep. of Germany ....... 3533912

[51] Int. Cl.⁴ .............................................. A61B 5/02
[52] U.S. Cl. ..................................... 128/672; 128/687
[58] Field of Search .............. 128/672, 687, 695, 696, 128/700, 706, 708, 710, 714, 689, 677, 680, 690, 705

[56] References Cited

U.S. PATENT DOCUMENTS

| 3,095,872 | 7/1963 | Tolles | 128/672 |
|---|---|---|---|
| 3,132,643 | 5/1964 | Baum et al. | 128/672 |
| 3,878,833 | 4/1975 | Arneson et al. | 128/672 |
| 4,000,461 | 12/1976 | Barber et al. | 128/708 |
| 4,026,277 | 5/1977 | Toda et al. | 128/680 |
| 4,144,526 | 4/1979 | Bargenda et al. | 128/706 |
| 4,195,642 | 4/1980 | Price et al. | 128/689 |
| 4,215,698 | 8/1980 | Nuwayser | 128/734 |
| 4,216,462 | 8/1980 | McGrath et al. | 128/710 |
| 4,224,948 | 9/1980 | Cramer et al. | 128/690 |
| 4,232,682 | 11/1980 | Veth | 128/689 |
| 4,240,442 | 12/1980 | Andreson et al. | 128/708 |
| 4,245,648 | 1/1981 | Trimmer et al. | 128/672 |
| 4,258,719 | 3/1981 | Lewyn | 128/690 |
| 4,301,808 | 11/1981 | Taus | 128/687 |
| 4,342,317 | 8/1982 | Axelgaard | 128/421 |
| 4,393,877 | 7/1983 | Imran et al. | 128/705 |
| 4,501,281 | 2/1985 | Furukawa | 128/677 |
| 4,537,200 | 8/1985 | Widrow | 128/696 |
| 4,617,938 | 10/1986 | Shimoni et al. | 128/708 |
| 4,664,127 | 5/1987 | Ikeyama | 128/689 |
| 4,688,597 | 8/1987 | Inahara | 128/695 |
| 4,717,548 | 1/1988 | Lee | 128/635 |
| 4,742,831 | 5/1988 | Silvian | 128/710 |

FOREIGN PATENT DOCUMENTS

| 1163327 | 3/1984 | Canada | 128/677 |
|---|---|---|---|
| 2642025 | 3/1977 | Fed. Rep. of Germany . | |
| 2750646 | 5/1979 | Fed. Rep. of Germany . | |
| 217422 | 1/1985 | Fed. Rep. of Germany | 128/689 |

Primary Examiner—Lee S. Cohen
Assistant Examiner—David Shay
Attorney, Agent, or Firm—Toren, McGeady & Associates

[57] ABSTRACT

A blood pressure measuring appliance having a pulse beat detector responding to arterial pulse beats, an ECG signal detector and a time measuring apparatus which ascertains the time intervals between peaks of a predetermined type of the ECG signal detected by the ECG signal detector, preferably its R-peaks, and pulse beats in each case following the R-peaks and detected by the pulse beat detector. A display apparatus displays a datum representing the duration of the ascertained time intervals as blood pressure information. The blood pressure measuring appliance must merely be calibrated initially, for example, with the aid of a sphygmomanometer, in blood pressure values. The inflatable bag can be eliminated for further blood pressure measurements.

6 Claims, 2 Drawing Sheets

BLOOD PRESSURE MEASURING APPLIANCE

BACKGROUND OF THE INVENTION

1. Field of the Invention

The invention relates to a blood pressure measuring appliance, and particularly, to an appliance having a pulse beat detector responding to arterial pulse beats, an electrocardiograph signal detector and a blood pressure measuring and indicating apparatus.

2. Description of Related Art

Blood pressure is ordinarily measured by means of an inflatable bag connected to a mercury manometer, according to the method of Riva-Rocci. The inflated bag ties off the upper arm so that the arm artery permits no more blood to flow therethrough. On reduction of the bag pressure the blood is again forced through the slowly opening artery. Then, as a result of turbulent flow, a noise occurs to which it is possible to listen with a stethoscope. The pressure read off on the manometer corresponds, on commencement of the turbulent flow, to the systolic blood pressure. When, upon further pressure reduction in the bag, the artery opens completely, the turbulent flow changes into a laminar flow and the heard sound or noise disappears. The pressure then read off on the manometer corresponds to the diastolic blood pressure. In this measuring method the accuracy of measurement depends upon the existing physiological conditions of the patient and the hearing capacity of the physician.

It is known from "Medical & Biological Engineering & Computing", September 1981, pages 671, 672, that the pulse beat transit time varies with the blood pressure. This is utilized, in combination with a conventional blood pressure measurement bag, for the determination of the measurement moments for the systolic pressure and the diastolic pressure. The time is ascertained between the R-peak of an ECG signal detected by means of an ECG signal detector and the arrival of the pertinent pulse beat at the location of a pulse beat detector. The systolic pressure is read off at the moment of maximum time delay on the manometer of the bag. The measurement moment for the diastolic pressure is ascertained in dependence upon the speed of variation of the transit times of successive pulse beats. The fact is utilized that the transit time of successive pulse beats remains constant after the diastolic pressure is reached. In the known blood pressure measuring appliance the actual blood pressure measurement takes place according to the bag method of Riva-Rocci.

The invention is directed towards provision of a blood pressure measuring appliance which, after initial calibration, can measure the blood pressure without an inflatable bag.

SUMMARY OF THE INVENTION

On the basis of the blood pressure measuring appliance as initially explained, the blood pressure measuring and indicating apparatus is formed, in accordance with the invention, as a time-measuring apparatus which ascertains the time intervals between peaks of a predetermined nature of the ECG signal, detected by the ECG detector, and pulse beats in each case following the predetermined peaks and detected by the pulse beat detector, and indicates as blood pressure information, a datum representing the duration of the ascertained time intervals.

The invention makes use of the fact that a predetermined relationship, reproducible with adequate accuracy, exists between the transit time of the pulse beats and the blood pressure. After an initial calibration of the time measuring apparatus to mean values of systolic and diastolic blood pressures, which were ascertained on the patient, preferably by means of a sphygmomanometer by the method of Riva-Rocci, the blood pressure measurement can thereafter be carried out for this patient without sphygmomanometer.

It has proved sufficiently accurate if a linear relationship is assumed between the transit time of the pulse beats and the blood pressure. Thus, two measured values suffice for the calibration in order that differing measured values may be interpolated or extrapolated. The calibrated values can be ascertained mathematically from the previously measured values by adjustment of scale end values of a mechanical computer dial or by operation of a computer circuit. It is self-evident that even more complicated functional relationships between the transit time and the blood pressure can be taken into consideration, especially if a computer circuit is used.

The ECG signal detector and the pulse beat detector preferably each comprise a comparator which compares the amplitude, detected by the detector, of the ECG signal, especially its R-peak, and/or the pulse beat, with a threshold value. The ECG signal detector and the pulse beat detector each generator an impulse when the ECG signal or the amplitude of the pulse beat, as the case may be, exceeds the threshold value in a predetermined direction. The time measurement stage then ascertains the time interval corresponding to the blood pressure, in dependence upon the impulses of the detectors.

The maximum amplitudes of the ECG signal and of the pulse beat can fluctuate greatly from patient to patient. In order nevertheless to achieve constant measurement results, it is preferredly provided that the threshold value indicator of the ECG signal detector or of the pulse beat detector, as the case, comprises an averaging stage which generates a threshold value signal following the time mean value of the ECG signal or the pulse beat sequence. Thus the threshold value indicator adapts the threshold value, for example, to the direct current mean value of the ECG signal or the pulse beat. In order to make the threshold value signal additionally adjustable, for example by hand, an adjustable direct current level is expediently superimposed upon the threshold value signal.

The impulse generated by the ECG signal detector or the pulse beat detector can be generated, for example, by means of a monoflop triggerable by the comparator. In place of a monoflop, it is also possible to use a differentiation member connected before the signal input of the comparator. This configuration additionally has the advantage that the leading edge of the impulse can be allocated more exactly in time to the leading edge of the R-peak of the ECG signal or the pulse beat, and, on the other hand, flatter impulse leading edges no longer instigate any triggering action.

The ECG signal detector is preferably decoupled from the time-measuring apparatus through an optocoupler, in order to reliably preclude stimulation of the patient by interfering impulses fed back to the ECG electrodes and to minimize artifacts upon the time-measuring apparatus. For the same reason, the ECG signal detector forms a separate construction unit with a line independent working voltage source, for example a battery or the like, which is independent of the voltage supply of the blood pressure measuring appliance.

Both above and below, it is to be understood that an ECG signal detector means any apparatus which generates a signal allocated to a predetermined peak of the ECG signal. As well as by skin electrodes, the ECG signal can be tapped from the patient by ultra-sonic Doppler methods, resistance measurements and sound detectors. For the generation of a signal representative of the pulse beats, it is possible to use photoelectric methods, ultrasonic Doppler methods, piezoelectric methods, resistance measurement methods, laser methods with infrared measurement, but also methods based upon dielectricity measurements, expansion measurements and upon the detection of infrasonic signals.

Active methods are preferred in which an active sensor delivers through a measured signal transmitter, a measured signal which varies in dependence upon blood pressure and is detected by a measured signal receiver. A preferred pulse beat detector of this kind comprises two measured signal receivers arranged apart from one another and from the measured signal transmitter, in order to facilitate the orientation of the pulse beat detector in relation to an artery. The two measured signal receivers are coupled to a selector circuit which responds to the signal amplitudes of the received measured signals and delivers the received measured signal with the greater amplitude, in each case, for the control of the time measuring apparatus. The selector circuit can for example be an OR circuit with biassed diodes. Since the maximum signal amplitudes can fluctuate greatly in dependence upon the measurement site, each of the two measured signal receivers comprises an amplification regulation circuit which keeps constant the mean direct-current voltage level of the measured signal fed to the selector circuit.

The pulse beat detector and also the time-measuring apparatus are expediently operated independently of line voltage from a battery or a rechargeable accumulator. In order to keep the current consumption of the pulse beat detector as low as possible, the measured signal transmitter of the sensor is worked in pulsed operation. Pulsed operation further has the advantage, in photoelectrically working measured signal receivers, that the influence of artificial light amplitude-modulated in the tempo of the line voltage frequency, can easily be suppressed without additional circuitry measures, for example, band-stop filters. The pulsed frequency is preferably selected equal to twice the line frequency. The output signal of impulse form of the measured signal receivers is smoothed in an impulse amplitude demodulator.

The measured signal transmitter is preferably an infrared luminescence diode, while the measured signal receivers are each formed as infrared photodiodes. In order to improve the accuracy of measurement of such a sensor, the infrared luminescence diode is preferably fed from a constant current source, especially in impulse form. Current/voltage converters are connected to the infrared photodiodes. Such converters have a very low input resistance, whereby the photodiode works in short-circuit operation, its output current is proportional to the received light intensity and also interference excitations of the supply leads are made ineffective.

The time-measuring circuit is preferably a microprocessor circuit. The measurement results are expediently indicated in a liquid crystal display, in order to save energy. The microprocessor circuit stores in its memory the measured values ascertained in the initial calibration and converts the measured transit times of the pulse beats into blood-pressure values. Further data, for example the pulse frequency, can be ascertained from the signals delivered by the detectors and displayed. Furthermore, with the aid of the microprocessor it is possible to determine upward and downward limit values of the blood pressure and the pulse frequency on overstepping of which the passed limit value appears on the display and in addition, in the case of prior permission of the user, an alarm is activated.

In order to keep the current consumption of the microprocessor circuit low, the time normally required for the time comparison is preferably realized not in the form of a program routine of the microprocessor but rather, by an additional quartz-stabilized timer circuit which the microprocessor governs in interrupt-request operation. The signals of the ECG signal detector and of the pulse beat detector are temporarily stored in a temporary store, likewise separate from the microprocessor, until they are processed by the microprocessor.

The various features of novelty which characterize the invention are pointed out with particularity in the claims annexed to and forming a part of this disclosure. For a better understanding of the invention, its operating advantages and specific objects attained by its use, reference should be had to the accompanying drawings and descriptive matter in which there are illustrated and described preferred embodiments of the invention.

DETAIL DESCRIPTION OF THE DRAWINGS

Figure 1:
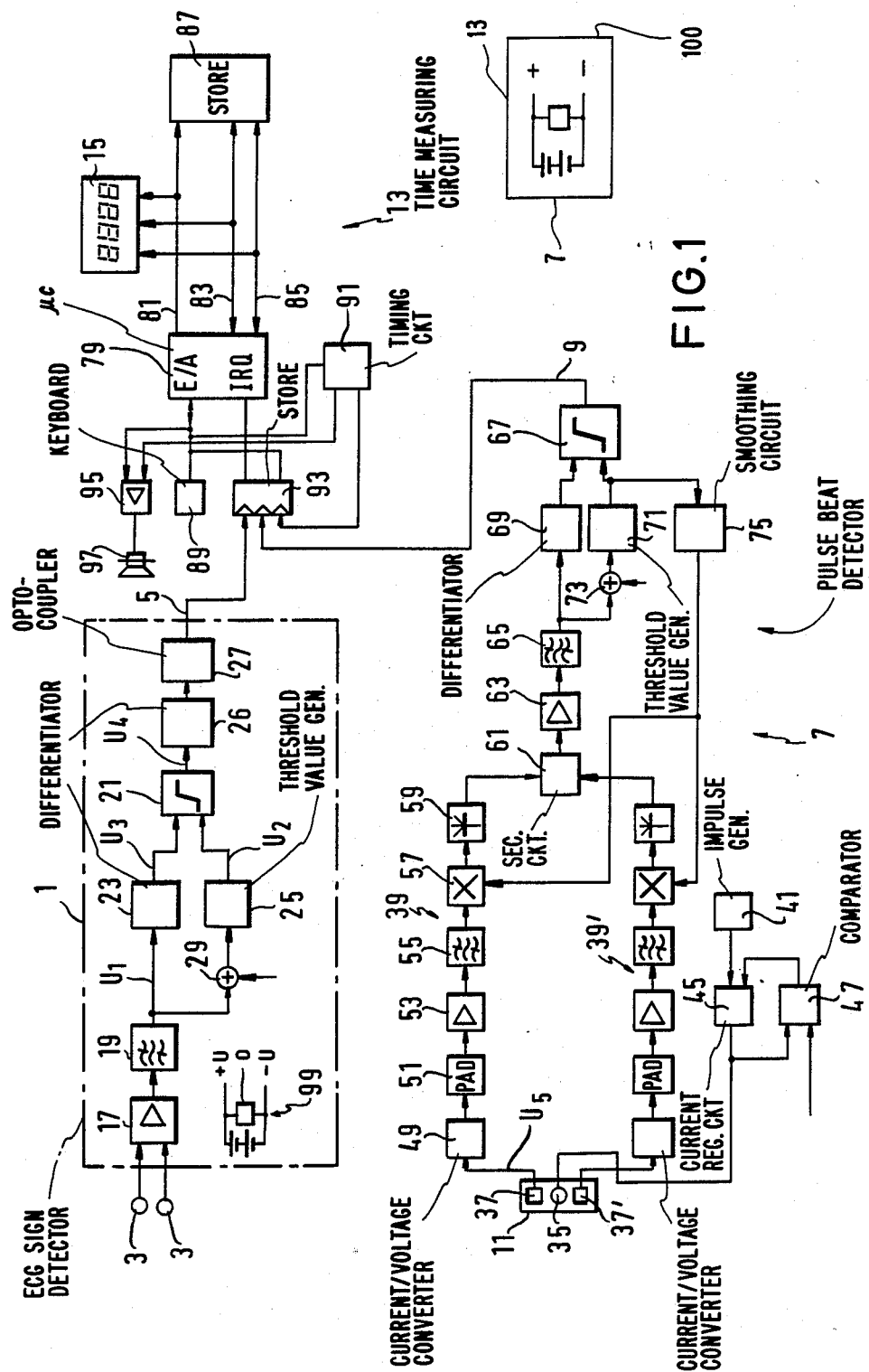
FIG. 1 shows a block circuit diagram of a blood-pressure measuring appliance according to the invention.

The blood pressure measuring appliance comprises an ECG signal detector 1 with skin-contact electrodes 3 which generates at its output 5, for each R-peak of the ECG signal, an impulse in a chronologically defined position in relation to the R-peak. A pulse beat detector 7 generates at its output 9, for each pulse beat following upon the R-peak, an impulse with fixed time relationship to the leading edge of the pulse beat. The pulse beat detector 7, possibly merely its sensor 11, is preferably held on an arm band and responds to arterial pressure fluctuations of the lower arm or another suitable part of the body. The impulses generated by the ECG signal detector 1 and the pulse beat detector 7 are fed to a time-measuring circuit 13 which ascertains the time interval between mutually associated impulses of the two detectors 1, 7 and, in dependence upon this time interval, displays a value representative of the blood pressure in a digital display apparatus 15, for example a liquid crystal display unit. The blood pressure measuring appliance here makes use of the fact that the blood pressure, which can be measured by the sphygmomanometer method of Riva-Rocci, is dependent in a predetermined manner upon the transit time of the pulse beat triggered by the R-peak of the cardiac action potential.

The ECG signal detector 1 comprises an input amplifier 17 connected with the ECG electrodes 3 and having an amplification factor of about 1000, and a band-pass filter 19 connected to the amplifier 17. The band-pass filter 19 is formed as an active filter, its pass band extending from about 7 to 40 Hz. The band-pass filter 19 eliminates artefacts and noise of the electrodes 3 and other interference signals received through the electrodes. A comparator 21, for example a Schmitt-Trigger, is connected with its one input through a differentiating member 23 to the band-pass filter 19 and with its other input to a threshold value generator 25. The differentiating member 23 generates impulses according to the edges of the ECG signal peaks, the amplitude of these impulses being compared with the signal generated by the threshold value generator 25. The threshold value is set so that only the differentiated signal of the leading edge of each R-peak exceeds the threshold value. The comparator 21 thus gives off a narrow impulse, for each leading edge of the R-peak, which is shortened in time by means of a differentiator 26 and fed through an opto-coupler 27 to the output 5. Since the input amplitude of the amplifier 17 can fluctuate greatly in dependence upon the fitting site of the electrodes, the threshold value generator 25 contains an averaging stage which adapts or readjusts the threshold value signal fed to the comparator 21 for comparison to the direct current mean value of the ECG signal. The ECG signal fed to the threshold value generator 25 for averaging is superimposed in a summing circuit 29 upon an adjustable reference direct current voltage level.

Figure 2:
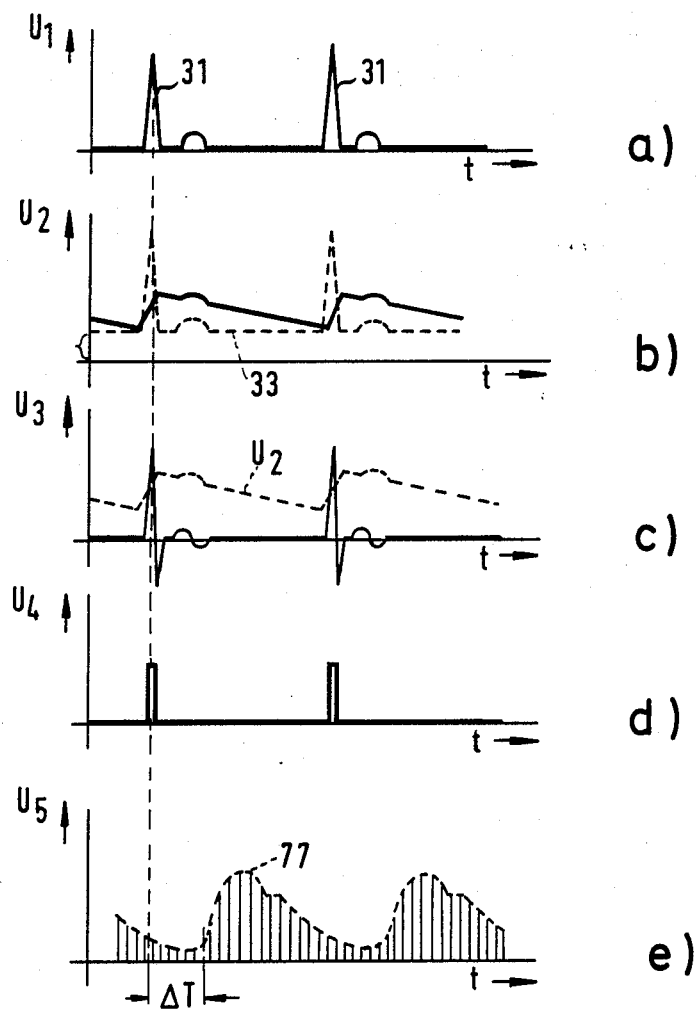
FIGS. 2a to 2e show time diagrams of signals which appear at different points of the block circuit diagram in FIG. 1.

FIG. 2a shows the ECG signal $U_1$ fed to the differentiating member 23 and supplied by the band-pass filter 19. The R-peaks are designated by 31 in FIG. 2a. FIG. 2b shows, with a curve 33 shown in dashed lines, the ECG signal $U_1$ from FIG. 2a after superimposition of the adjustable reference level in the summing circuit 29. The threshold value signal $U_2$, obtained by averaging the signal 33 and still recognizably following the ECG signal $U_1$ in order to ensure a sufficiently rapid speed of adaptation of the threshold value, is represented in solid lines in FIG. 2b. FIG. 2c shows in solid lines the differentiated ECG signal $U_3$ and shown in dashed lines, in comparison therewith, the threshold value signal $U_2$ fed together with the signal $U_3$ to the comparator 21. The needle impulses of the signal $U_3$, corresponding to the leading edges of the R-peaks 31, generate needle impulses $U_4$ at the output of the comparator 21.

The sensor 11 of the pulse beat detector 7 comprises an infrared luminescence diode 35 and two infra-red photodiodes 37, 37' arranged on mutually opposite sides of the diode 35 and spaced therefrom. The photodiodes 37, 37' detect the infra-red light emitted by the luminescence diode 35 and reflected according to the state of filling of the artery. The pulse beat travelling past beneath the sensor 11 momentarily increases the state of filling of the artery and leads to a fluctuation of intensity of the reflected light. The output signals of the photodiodes 37 and 37' are processed further in separate channels 39 and 39' and the signal of greater amplitude in each case is automatically selected at the output of the channels 39, 39'. Thus the orientation of the sensor 11 in relation to the artery is facilitated.

The luminescence diode 35 is operated from an impulse generator 41 through a current regulating circuit 45 with current of impulsed form of constant impulse amplitude. A comparator circuit 47 controlling the current-regulating circuit 45 compares the actual value of the impulse amplitudes with a preferably adjustable ideal or nominal value. Due to the impulsed operation of the luminescence diode 35, the current consumption of the blood pressure measuring appliance, preferably operated from a battery or rechargeable accumulator, is reduced. The current-regulating circuit 45 ensures constant luminous intensity of the transmitted infrared light impulses. The impulse frequency of the impulse generator 41 is made equal to twice the line voltage frequency, that is 100 Hz for a line frequency of 50 Hz. In this way, without need to use a notch filter, the influences of artificial light upon the photo-diodes 37, 37' can be eliminated by ordinary band-pass filters.

A current-to-voltage converter 49, for example an amplifier with very low input impedance, is connected to the photodiode 37. The converter 49 short-circuits the photodiode 37 for interference voltages and thus is controlled in dependence upon the output current of the photodiode 37. In short-circuit operation, the output current of the photodiode 37 is in linear proportion to the received light intensity. To the current/voltage converter 49, there is connected a pulse amplitude demodulator 51 which delivers to a buffer amplifier 53 an impulse output signal of the photodiode 37 amplitude-modulated according to the envelope curve of the pulse beat. The buffer amplifier 53 has an amplification factor of about 60. To the buffer amplifier 53, a band-pass filter 55 is connected, the pass band of which reaches from about 4 to 45 Hz. The band-pass filter 55 eliminates interference deriving from the connecting cable of the sensor 11 and from extraneous light influences. To the band-pass filter 55, there is connected, through a multiplier 57, a rationalizer 59, for example a two-way rectifier, which, irrespective of the sign of the signals delivered through the band-pass filter 55, delivers a signal following the pulse beat amplitude with constant sign to a selector circuit 61. The selector circuit 61, which may be a diode circuit after the style of an OR-gate with biassed diodes, selects from the two signals supplied through the channels 39, 39' the signal with the greater amplitude in each case. The multiplier 57 is a component of an amplification regulating circuit which keeps the direct current mean value of the signal delivered to the selector circuit 61 constant after the style of an automatic amplification regulation circuit. The channel 39' connecting the photodiode 37' with the selector circuit 61 is assembled identically with the channel 39 and therefore is not to be explained further.

A band-pass filter 65, the pass band of which reaches from about 5 Hz to 35 Hz and further constricts the pass band of the band-pass filter 55, is connected to the selector circuit 61 through an amplifier 63. The impulse at the output 9 designating the pulse beat is generated by means of a comparator 67, for example a Schmitt-Trigger, corresponding to the ECG signal detector 1. The signal input of the comparator 67 is connected for this purpose through a differentiating member 69, corresponding to the differentiating member 23, to the band-pass filter 65. The threshold value input of the comparator 67 is connected with a threshold value generator 71 which generates a threshold value signal following the direct current mean value of the pulse beat signal delivered by the band pass filter 65. The pulse beat signal is fed to the threshold value generator 71 by way of a summing circuit 73 in which it is superimposed upon a preferably adjustable direct current level. The manner of operation of the circuit consisting of the components 67 to 73 corresponds to the circuit of the components 21 to 25 and 29 of the ECG signal detector 1.

The threshold value generator 71, through a smoothing circuit 76, delivers a control signal to the multiplier 57 in both channels. The smoothing circuit 75 delivers a signal approximately following the direct current average value of the output of the threshold value generator 71, for regulation of amplification in the two channels 39, 39'.

FIG. 2e shows the impulse signal $U_5$ of the photodiode 37, amplitude modulated according to the pulse beats. The envelope curve available at the output of the rationalizer 59 and representative of the pulse beat is shown in dashed lines at 77 in FIG. 2e. The circuit formed from the parts 67 to 73 generates the output impulse at the output 9 with the beginning of the step leading edge of the pulse beat. The time difference between the R-peak 31 in FIG. 2a and the associated pulse beat, representing the blood pressure, is designated in FIG. 2e by $\Delta T$.

The time measuring circuit 13 comprises a microcomputer 79 which is connected through an address bus 81, a data bus 83 and a status bus 85 with a programme and data store 87 and the alpha-numerical display apparatus 15. The microcomputer 79 is operable through an input IRQ in interrupt-request operation and connected with a keyboard 89 through which data explained later in greater detail can be introduced. In order to keep the current consumption of the microcomputer 79 low, the time standard necessary for the time comparison is not realized by a program loop, but is formed by a timing circuit 91 working independently of the interrupt operation of the microcomputer 79. The timing circuit 91 comprises a continuously rotating counter which counts the timing pulses of a quartz-stabilized timing pulse generator. The microcomputer 79 counts only the overflows of the counter and interrogates the momentary state of the counter for the time comparison of the impulses occurring at the outputs 5 and 9. For this purpose, the timing circuit 91 is connected with a temporary store 93 which also temporarily stores the impulses delivered by the ECG signal detector 1 and the pulse beat detector 7, for transmission to the microcomputer 79.

From the calibration values stored in the store 87, the microcomputer 79 calculates a blood pressure value in linear dependence upon the measured time interval $\Delta T$. In the simplest form, the blood pressure value is calculated according to a linear equation given by two calibrated values. The calibrated values are expediently the values ascertained by means of an inflatable Riva-Rocci bag for the systolic and diastolic blood pressures.

The microcomputer 79 can be utilized to monitor blood pressure limit values and, on overstepping of the limit values introduced through the keyboard 89, switches on a driver amplifier 95 of an acoustic alarm 97. The alarm sound can be generated by the stage 91. The acoustic alarm 97 can also be used to render the systolic sound or the diastolic sound audible. Furthermore the microcomputer 79 and its digital display apparatus 15 can be utilized for the measurement and display of the heart beat frequency. The manner of operation is switched over by means of the keyboard 89, through which the calibrated values and the limit values are also introduced.

The voltage supply of the time measuring circuit 13 and of the pulse beat detector 7 is represented at 100 and may preferably be a battery or a rechargeable accumulator. The ECG signal detector 1 is supplied with voltage from a voltage source represented at 99, for example a battery, independently of the voltage supply 100 of the time measuring circuit 13 and of the pulse beat detector 7. In combination with the opto-coupler 27, in this way the patient is optimally protected against the feedback of heart-stimulating interference impulses to the ECG electrode 3.

While specific embodiments of the invention have been shown and described in detail to illustrate the application of the inventive principles, it will be understood that the invention may be embodied otherwise without departing from such principles.

What we claim is:

1. A blood pressure measuring appliance comprising:
   (a) a pulse beat detector for detecting arterial pulse beats, the pulse beat detector comprising an active sensor having a measuring signal transmitter connected to an impulse generator having an impulse frequency selected to be equal to an integral multiple greater than or equal to twice a line voltage frequency, delivering a measuring signal of impulse form and two measuring signal receivers spaced from one another and from the measuring signal transmitter, which respond to the measuring signal in dependence upon the pulse beat, and wherein the measuring signal receivers are coupled to a selector circuit which is responsive to signal amplitudes of the received measuring signals;
   (b) an ECG signal detector having at least two ECG electrodes for determination of ECG signals, and an evaluation circuit selectively responding to ECG signal peaks of a predetermined type and amplifying the ECG signals of the ECG electrodes, the ECG electrodes being contactable to skin;
   (c) a time measuring means for determination of time intervals between a predetermined ECG signal peak acquired by the ECG signal detector and the pulse beats acquired by the pulse beat detector, respectively, following the predetermined peak, the selector circuit delivering the received measuring signal having a greater of the signal amplitudes in each case for controlling said time measuring means;
   (d) a blood pressure display means for displaying the duration of time interval determined by the time measuring means as blood pressure information;
   (e) a signal transmission arrangement optically coupling the evaluation circuit of the ECG signal detector with the time measuring means;
   (f) a first operational voltage source supplying exclusively the ECG signal detector including the optical signal transmission arrangement; and
   (g) a second operational voltage source supplying the remaining components of the blood pressure measuring appliance independent of the first operational voltage source.

2. A blood pressure measuring appliance according to claim 1, wherein the selector circuit is coupled through separate amplitude control stages to the two measuring signal receivers, and wherein an averaging stage is coupled to the selector circuit which delivers to the separate amplitude control stages an amplitude control signal dependent on an average value over time of the selected received measuring signal, said control signal maintaining an amplitude mean value of the received measuring signal delivered by the selector circuit substantially constant at a predetermined value.

3. A blood pressure measuring appliance according to claim 1, wherein pulse amplitude demodulators are respectively connected between said measuring signal receivers and the selector circuit and band-pass filters are respectively connected between the pulse amplitude demodulators and the selector circuit.

4. A blood pressure measuring appliance according to claim 3, wherein each of the band-pass filters has a pass band covering a span of approximately 4 Hz to 45 Hz.

5. A blood pressure measuring appliance according to claim 1, wherein the measuring signal transmitter is formed as an infrared luminescence diode and the measuring signal receivers are each formed as infrared photodiodes, wherein the infrared luminescence diode is fed from a constant current source and wherein the infrared photodiodes have respective current-to-voltage converters connected thereto.

6. A blood pressure measuring appliance according to claim 1, wherein said time measuring means is formed as a microprocessor circuit which is connected through a temporary stored to the ECG signal detector and the pulse beat detector, and wherein a quartz-stabilized timer circuit is connected to the microprocessor circuit for the formation of a measuring time standard for the microprocessor circuit.

* * * * *